US010001464B2

United States Patent
Kronenberger et al.

(10) Patent No.: US 10,001,464 B2
(45) Date of Patent: Jun. 19, 2018

(54) BEACH DETECTION SENSORS FOR VIBRATORY SEPARATOR

(71) Applicant: M-I L.L.C., Houston, TX (US)

(72) Inventors: Edward Kronenberger, Houston, TX (US); Venkata Amaravadi, Houston, TX (US); Colin Stewart, Houston, TX (US)

(73) Assignee: M-I L.L.C., Houston, TX (US)

( * ) Notice: Subject to any disclaimer, the term of this patent is extended or adjusted under 35 U.S.C. 154(b) by 633 days.

(21) Appl. No.: 14/317,903

(22) Filed: Jun. 27, 2014

(65) Prior Publication Data
US 2015/0377020 A1  Dec. 31, 2015

(51) Int. Cl.
| | |
|---|---|
| *E21B 49/08* | (2006.01) |
| *G01N 33/18* | (2006.01) |
| *G01N 27/22* | (2006.01) |
| *E21B 21/06* | (2006.01) |
| *G01N 25/56* | (2006.01) |
| *B07B 1/42* | (2006.01) |
| *B07B 13/18* | (2006.01) |
| *B03B 5/06* | (2006.01) |
| *B03B 13/04* | (2006.01) |
| *B03B 13/00* | (2006.01) |

(Continued)

(52) U.S. Cl.
CPC ............ *G01N 33/18* (2013.01); *E21B 21/065* (2013.01); *G01N 25/56* (2013.01); *B01D 33/0376* (2013.01); *B01D 37/00* (2013.01); *B01D 37/043* (2013.01); *B01D 37/045* (2013.01); *B03B 5/06* (2013.01); *B03B 13/00* (2013.01); *B03B 13/04* (2013.01); *B07B 1/42* (2013.01); *B07B 13/18* (2013.01); *G01N 27/223* (2013.01)

(58) Field of Classification Search
CPC ....... E21B 21/065; E21B 49/08; G01N 25/56; G01N 27/223; G01N 33/18; B03B 5/06; B03B 13/00; B03B 13/04; B07B 1/42; B07B 13/18; B01D 33/0376; B01D 37/00; B01D 37/043; B01D 37/045
See application file for complete search history.

(56) References Cited

U.S. PATENT DOCUMENTS

| | | |
|---|---|---|
| 7,571,817 B2 | 8/2009 | Scott et al. |
| 2002/0079251 A1 | 6/2002 | Schulte et al. |

(Continued)

FOREIGN PATENT DOCUMENTS

| | | |
|---|---|---|
| EP | 825895 A1 | 3/1998 |
| EP | 825895 B1 | 12/1998 |

OTHER PUBLICATIONS

International Preliminary Report on Patentability for PCT/US2015/038170 dated Jan. 5, 2017.

(Continued)

*Primary Examiner* — Matthew O Savage
(74) *Attorney, Agent, or Firm* — David J. Smith

(57) ABSTRACT

An apparatus including a screen capable of separating solids from a liquid-solid mixture and a first probe disposed beneath the screen. The first probe is provided to determine a position of a beach between the liquid-solid mixture and separated solids. The apparatus may measure a property of a local volume of a probe disposed beneath a first separator deck. The probe may then send a first signal to database. Based on the signal a location of a beach may be determined.

20 Claims, 12 Drawing Sheets

(51) Int. Cl.
    *B01D 37/04*          (2006.01)
    *B01D 33/03*          (2006.01)
    *B01D 37/00*          (2006.01)

(56) References Cited

U.S. PATENT DOCUMENTS

| | | |
|---|---|---|
| 2004/0129612 A1 | 7/2004 | Decenso |
| 2005/0242002 A1 | 11/2005 | Stone et al. |
| 2005/0242009 A1* | 11/2005 | Padalino ............ B01D 33/0376 |
| | | 210/86 |
| 2006/0243643 A1 | 11/2006 | Scott et al. |
| 2012/0118798 A1 | 5/2012 | Scott et al. |

OTHER PUBLICATIONS

International Search Report and Written Opinion issued in PCT/US2015/038170 dated Sep. 18, 2015, 13 pages.

* cited by examiner

BEACH DETECTION SENSORS FOR VIBRATORY SEPARATOR

BACKGROUND

Separators may be used in various industries such as the food industry, cleaning industry, waste water treatment, and others. The vibratory separator may include a generally horizontal table or an angled table with a perforated filter screen bottom. Fluid is deposited at the feed end of the vibratory separator. As the fluid travels along the length of the vibrating table, the fluid falls through the perforations in a separation screen to a reservoir below, leaving the solid particulate material behind. The vibrating action of the vibratory separator table conveys solid particles left behind to a discharge end of the separator table. The above described apparatus is illustrative of one type of vibratory separator known to those of ordinary skill in the art. In alternate vibratory separators, the feed end of the separator may be relatively closer to the ground than the discharge end. In such vibratory separators, the angle of inclination may require the movement of particulates in a generally upward direction. In still other vibratory separators, the table may not be angled, thus the vibrating action of the separator alone may enable particle/fluid separation. Regardless, table inclination and/or design variations of existing vibratory separators should not be considered a limitation of the present disclosure.

In the oilfield industry, drilling fluid, often called "mud," serves multiple purposes in the industry. Among its many functions, the drilling mud acts as a lubricant to cool rotary drill bits and facilitate faster cutting rates. Typically, the mud is mixed at the surface and pumped downhole at high pressure to the drill bit through a bore of the drill string. Once the mud reaches the drill bit, it exits through various nozzles and ports where it lubricates and cools the drill bit. After exiting through the nozzles, the "spent" fluid returns to the surface through an annulus formed between the drill string and the drilled wellbore.

In addition to cooling the bit, the drilling mud carries the cuttings away from the drill bit at the bottom of the borehole to the surface. As a drill bit pulverizes or scrapes the rock formation at the bottom of the borehole, small pieces of solid material are left behind. The drilling fluid exiting the nozzles at the bit acts to stir-up and carry the solid particles of rock and formation to the surface within the annulus between the drill string and the borehole. Therefore, the fluid exiting the borehole from the annulus is a slurry of formation cuttings in drilling mud. Before the mud can be recycled and re-pumped down through nozzles of the drill bit, the cutting particulates are removed by a separator, such as a vibratory separator.

DETAILED DESCRIPTION

Figure 1:
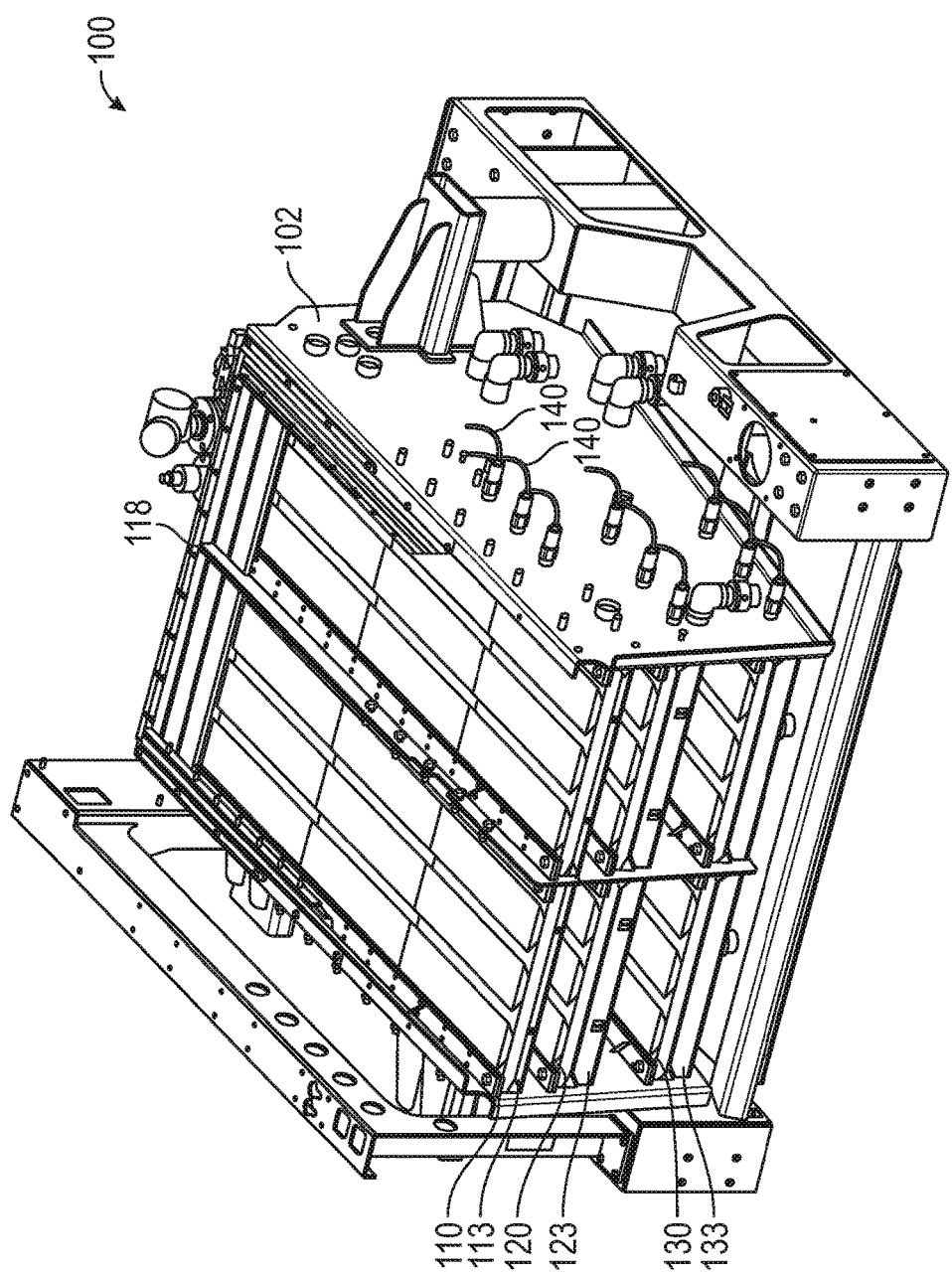
FIG. 1 shows a perspective view of a separator in accordance with embodiments of the present disclosure.

Embodiments disclosed herein generally relate to an apparatus and methods for determining a position of a beach during separation of solids from a fluid. In particular, embodiments of the present disclosure provide a separator having a probe disposed beneath the separator deck to monitor a position of the beach.

Monitoring the movement of fluid, e.g. wellbore fluid or drilling fluid, across a separator deck and/or screen, may be performed to ensure excess drilling fluid is not inadvertently discarded and improve the longevity of the separator deck. As used herein, the term "separator deck" refers to at least one screen disposed in a frame. According to some embodiments, a separator deck may include multiple screens. Each screen may be coupled to the separator by any means known in the art, for example, tracks, clamping systems, etc. Each separator deck as used herein may occupy a level of the separator. For example, the separator 100 shown in FIG. 1 includes three separator decks or levels: a top separator deck 110, a middle separator deck 120, and a bottom separator deck 130. One skilled in the art will understand that the number of separator decks disposed in a separator 100 is not intended to limit the scope of the present disclosure.

During separatory operations, a liquid-solid mixture or drilling fluid may be deposited onto a feed end of a vibratory separator. The liquid-solid mixture may form a "pool" comprising primarily the liquid-solid mixture on the feed end of the vibratory separator. As the liquid-solid mixture progresses across the separator deck, fluid may drain through a screen disposed in the separator deck leaving primarily solid matter to be discarded at a discharge end. The "beach" as used herein refers to a region where the pool of the liquid-solid mixture transitions to a region consisting of primarily solid matter. As used herein, the term "beach" may refer to a region and not a definite boundary line.

Embodiments disclosed herein relate to an apparatus and methods for determining a position of a beach. In particular, embodiments disclosed herein include disposing a probe below a screen or separator deck of a vibratory separator for determining the location of a beach. The probe may be used to determine if fluid (i.e. drilling fluid) passes through the separator deck in a region proximate the probe. That is, the probe may monitor a region proximate the probe to determine if liquid (i.e. drilling fluid) is present.

One or more probes may be used to determine changes in the amount of fluid, if any, that passes through the separator deck. The probes may be disposed proximate a desired beach location. According to some embodiments, the probe may be disposed at a position where the beach is not desired. For example, a first probe may be disposed at a location closer to a feed end than the desired beach. A second probe may be disposed at a location closer to the discharge end than the desired beach. A third probe may be disposed at the location of a desired beach. Based on the data collected from the probes, a location of the beach along the screen may be determined. The vibratory separator may be adjusted based on the determination of the location of the beach to affect the position of the beach. One skilled in the art will understand that the number and position of the probes is not intended to limit the scope of the present disclosure.

Figure 2:
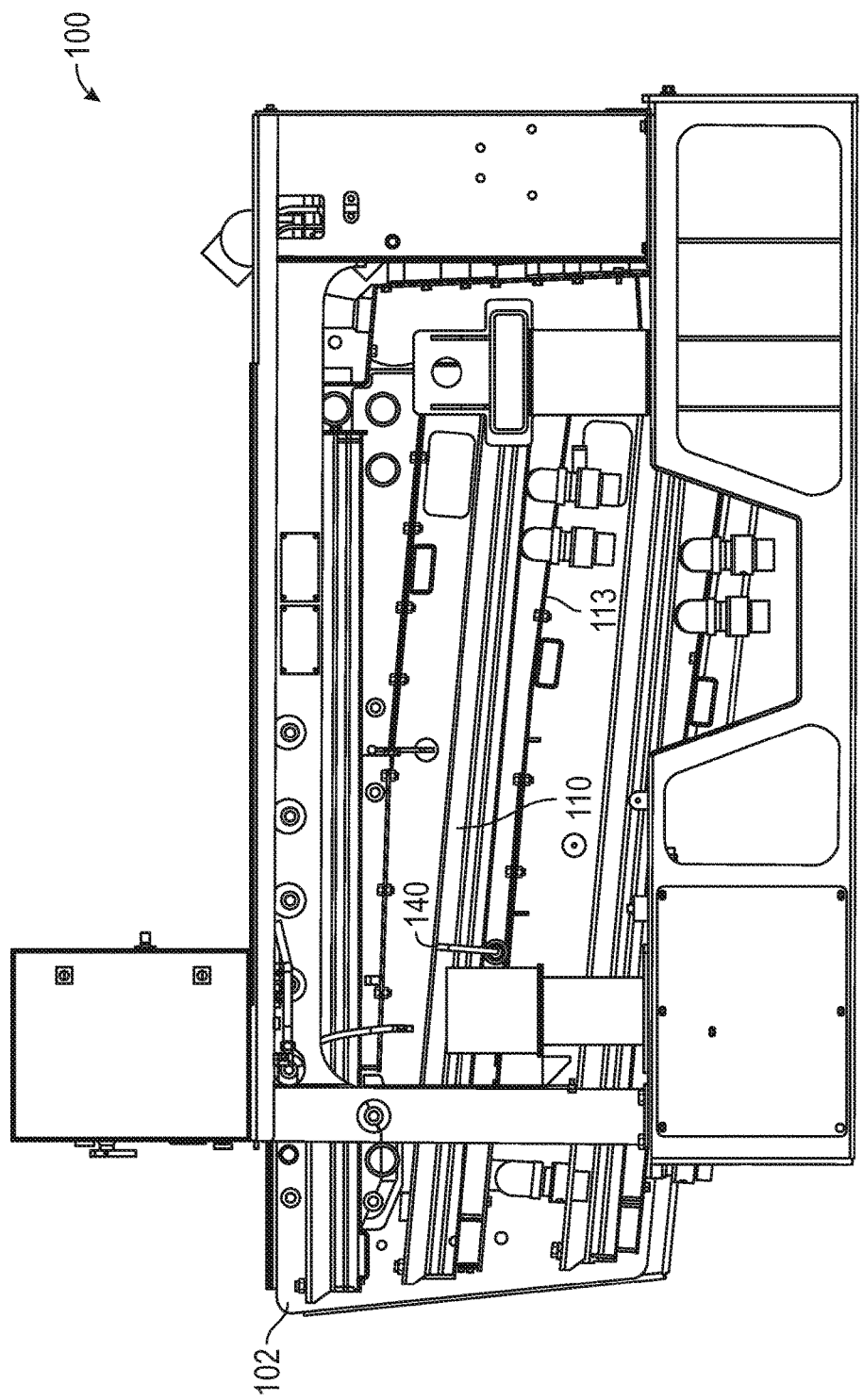
FIG. 2 shows a side view of a separator in accordance with embodiments of the present disclosure.
Figure 3:
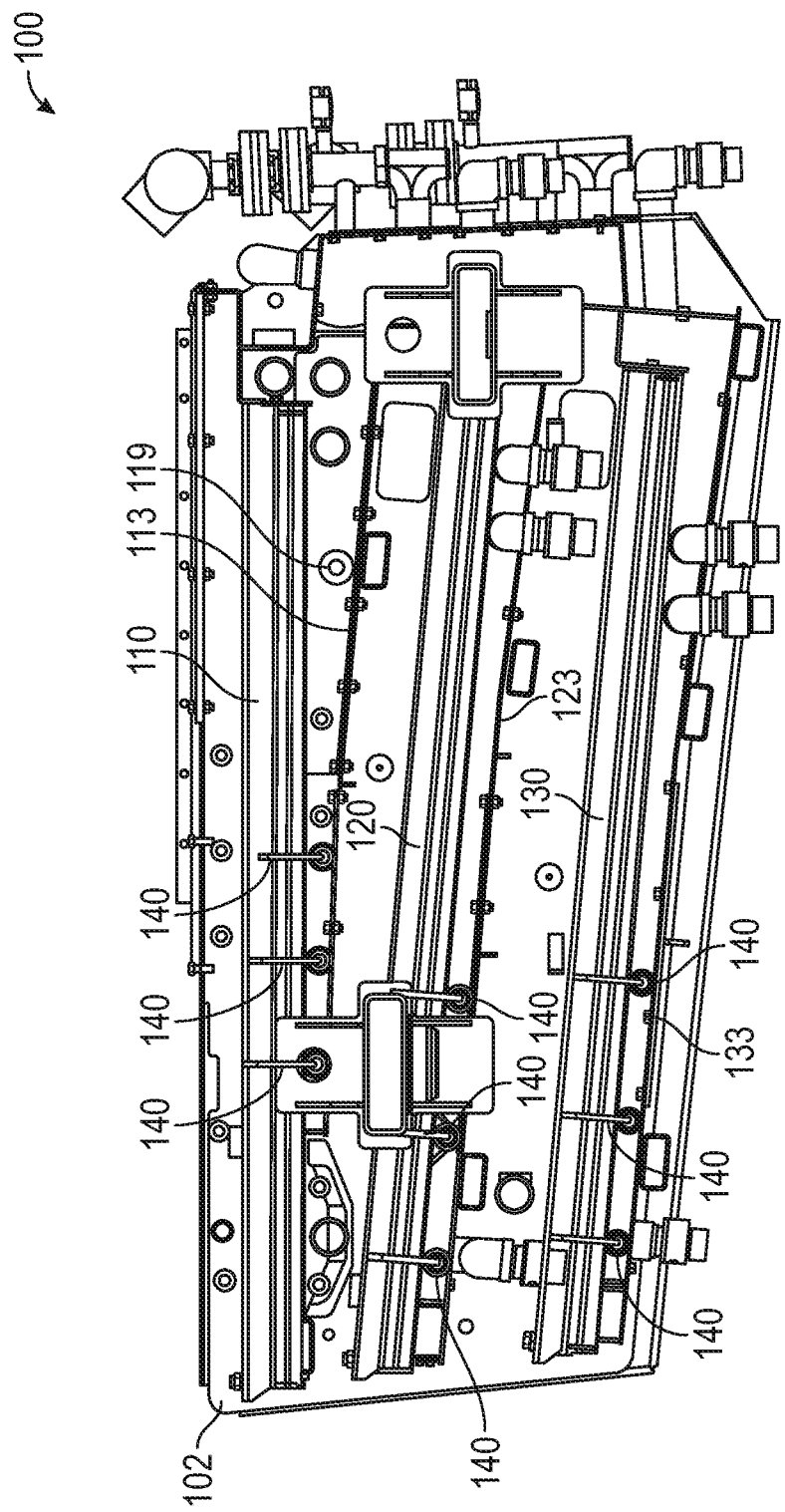
FIG. 3 shows a side view of a separator in accordance with embodiments of the present disclosure.

FIGS. 1-3 show a separator 100 in accordance with embodiments of the present disclosure. FIG. 1 shows the separator 100 without screens disposed therein. The separator 100 includes a separator deck 110 and a probe 140 disposed beneath the separator deck 110 for measuring at least one characteristic of a local volume i.e., a region proximate the probe 140 to determine the presence of fluid in the local volume. Additionally, one skilled in the art will understand that embodiments disclosed herein may be used with a variety of fluid/solid separation devices, for example, separators for food processing, separators for waste water treatment, etc. Further, while embodiments described herein may be in reference to applications in the oil and gas industry, the apparatus and methods described herein are limited to the oil and gas industry.

The probe 140 may determine a property of a region or volume proximate the probe 140 (herein referred to as a "local volume"). For example, as will be described in more detail below, the probe 140 may be used to determine a capacitance, heat capacity, temperature, pressure, or other property of a fluid (i.e. air and/or drilling fluid) present in a region or local volume. For example, the probe 140 may determine the capacitance of a gas or a liquid in the local volume. The probe 140 may determine a property of a region or volume by measuring a value of the property (e.g., capacitance value, heat capacity value, etc.) or the probe 140 may simply detect a change in property (e.g., an increase or decrease in capacitance).

The property may be used to determine what fluids (i.e. air and/or drilling fluid) are present within the local volume. For example, based on the property determined by probe 140, it may be determined that the local volume includes gas, liquid, or combinations of both. Based on the determined property, a specific type of fluid or gas may be determined. The size of the local volume may vary based on the probe 140 used and the location and orientation of the probe 140 within the separator. For example, the local volume may encompass a volume approximately 1 inch from the probe 140 along the length of the probe. For a cylindrical probe having a radius of approximately 0.10 inches, the local volume may have a radius of 1.10 inches, that extends the length of the probe. However, the length of the local volume may also vary. For example, the length of the local volume may be approximately equal to the length of the probe 140, approximately equal to a width or length of the separator deck 110, or a length shorter or longer than the probe 140, width or length of the separator deck 110. The example of the local volume above is provided for illustrative purposes and is not intended to be limiting. In some embodiments, the local volume may be more or less than 1 inch from the probe 140 and extend along the length of the probe.

The probe 140 may be positioned in or on the separator 100 to identify a presence (or lack thereof) of a liquid (i.e. a drilling fluid) in the local volume of the probe 140. For example, the probe 140 may be disposed near a desired location of a beach for monitoring the location of the beach. In some embodiments, the probe 140 may be positioned under the separator deck 110 such that fluid passing through the separator deck may enter the local volume or region proximate the probe 140. Accordingly, as fluid enters the region proximate the probe 140, i.e., the local volume, the probe 140 measures or detects at least one property of the filtered fluid entering or deposited in the local volume and/or deposited on the probe 140. Based on the presence of fluid in the local volume and/or contact or lack of contact of the fluid with the probe 140, a position or location of the fluid with respect to the separator deck 110 can be determined.

Referring to FIG. 2, probe 140 is provided beneath a separator deck 110 (i.e., beneath a screen of the separator deck) to determine a property of the local volume. Based on the property of the local volume, a user or operator may determine if fluid is present in the local volume. The probe 140 may be disposed proximate a desired or estimated beach location. For example, the probe 140 may be disposed at a desired beach location. According to some embodiments, the probe 140 may be disposed at a location where the beach is not desired. For example, the probe 140 may be disposed a short distance before and/or after the desired beach location. The desired beach location may be chosen or estimated based on the fluid to be filtered. For example, in drilling applications, the desired beach location may be chosen based on the type of formation being drilled, the type of mud used, the flow rate of the fluid entering the separator, acceptable particle size, fluid viscosity, fluid gel point, need to recover loss control material (LCM), and/or need to reject low gravity (fine particle) solids.

According to some embodiments a desired beach location may be about 75% of the length of a separator deck from a feed end of the separator. According to some other embodiments the desired beach location may be about 50%-95% of the length of a separator deck from the feed end. Although, reference to a distance from a feed end is provided, one having ordinary skill in the art will understand that a desired location of the beach may be determined from the discharge end, for example, a desired beach location may be about 25% of the length of a separator deck from a discharge end.

The probe 140 may be any probe known in the art to measure a property of a local volume. As the amount of fluid entering the local volume and/or being deposited on the probe 140 changes, so will the property of the local volume. According to some embodiments, the probe 140 may be a capacitance probe that measures the capacitance of a local volume of the probe 140. For example, a capacitance probe (e.g. Liquicap FMI151 from Endress+Hauser, Reinach, Switzerland; or Model 167 from Robertshaw Industrial Products, Maryville, Tenn.) may be used to measure capacitance of the local volume. The measured capacitance may correspond to an amount of fluid in the local volume of the probe, i.e. a higher capacitance may correspond to more fluid being deposited on the probe 140, while a lower capacitance may correspond to less fluid entering the local volume and/or being deposited on probe 140. A thermal diffusivity probe (e.g. FLT93 from Fluid Components International LLC, San Marcos, Calif.) may also be used to monitor the local volume. The thermal diffusivity probe may work by monitoring a change in temperature as well as the power/heat input of the probe 140 over a period of time to determine the thermal conductivity of the local volume.

According to some embodiments, an outer surface of the probe 140 may be coated with a non-stick compound such as polytetrafluroethylene (e.g, TEFLON, by DUPONT, Delaware), to prevent the filtered fluid from damaging or caking on a surface of the probe 140. As fluid enters the local volume and is deposited on the probe 140, a fluid layer or cake on the probe 140 may affect the accuracy of the probe 140 measurements, as the probe 140 measurements may reflect properties of the fluid layer, not the current properties of the local volume. Thus, the polytetrafluroethylene coating may allow fluid to be repelled from the surface of the probe 140 and enhance the accuracy of the probe 140 measurements.

Figure 13:
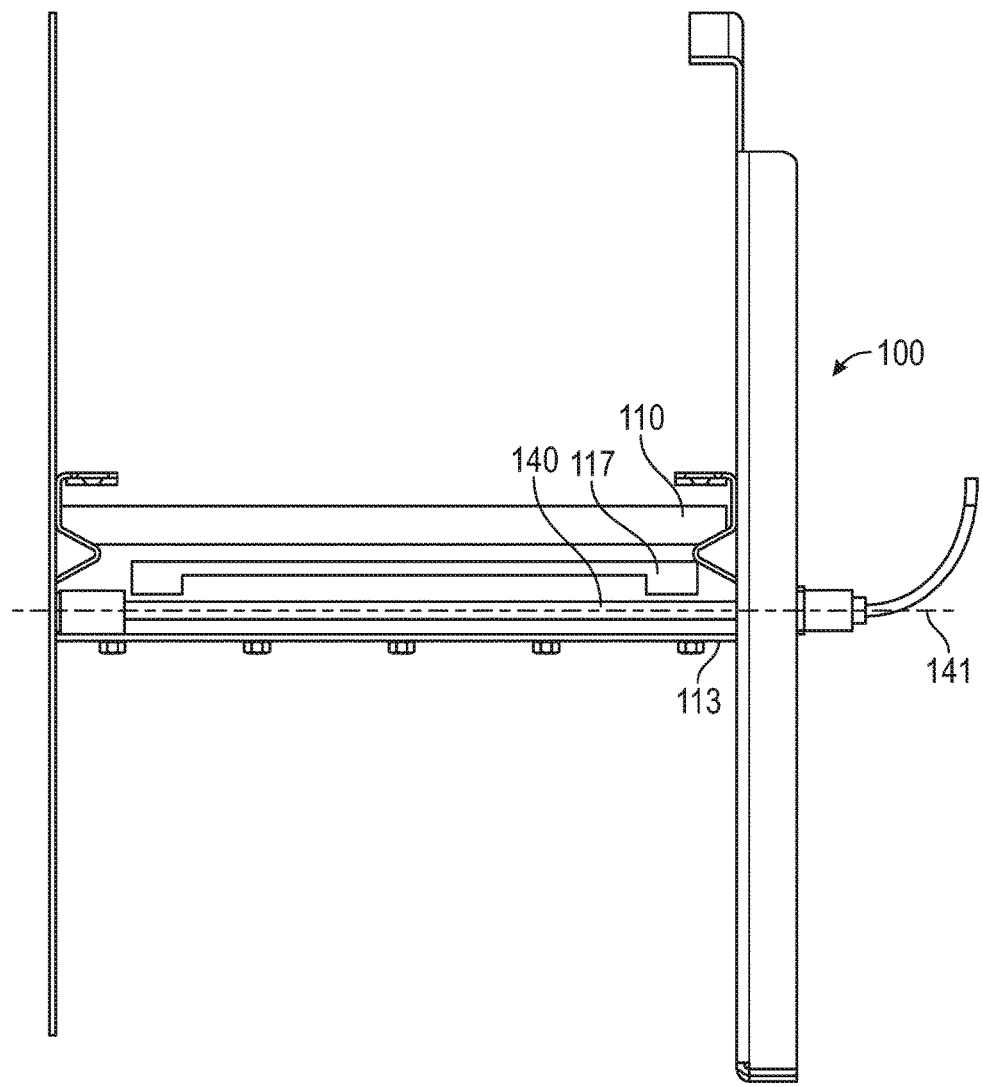

The probe 140 may be generally cylindrical in shape having a diameter that is less than the length of the probe 140. According to some embodiments the diameter of the probe may not be constant from a first end of the probe to a second end of the probe. According to some embodiments, a diameter of the probe may be about 0.6 inches. According to some embodiments, a diameter of the probe may be less than 1 inch. According to some embodiments, a diameter of the probe may be greater than one inch. As seen in FIG. 13, a central axis 141 of the probe may be defined as a longitudinal line that runs through the center of the probe 140. According to some embodiments, the central axis of the probe 140 is about parallel to a plane of the separator deck 110.

The probe 140 may be operatively coupled to an electronic control module (ECM) or database (not shown), which is configured to receive a signal from the probe 140 and display the signal to a user or operator. The signal will indicate to the user or operator a property of the local volume measured by the probe 140. Based on the signal, the user or operator may determine if fluid (i.e. air or drilling fluid) is present in the local volume. Based on the location of the probe 140 and the presence of fluid in the local volume, the location of a beach on separator deck 110 may be determined.

Figure 4:
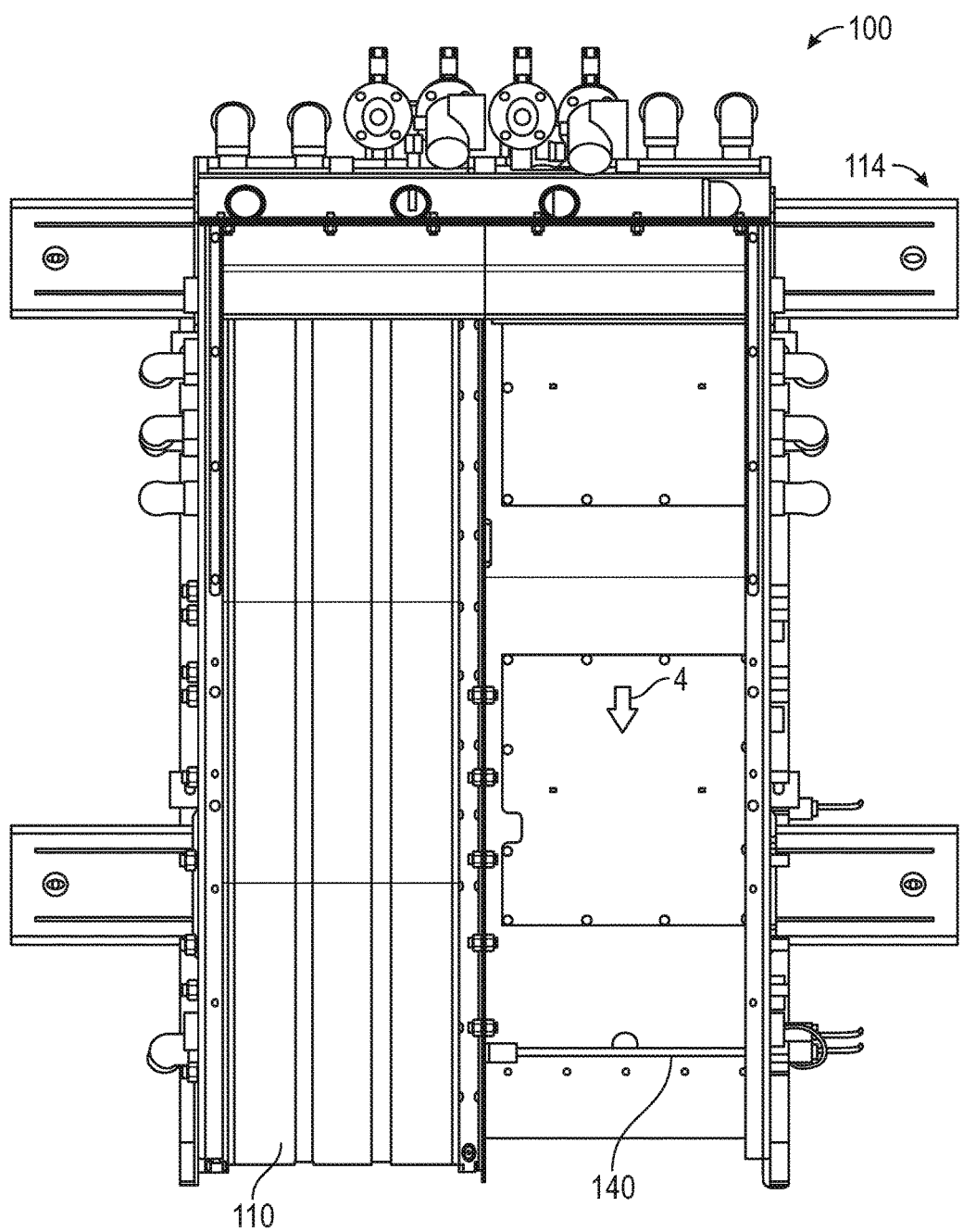
FIG. 4 shows a top view of a separator in accordance with embodiments of the present disclosure.

For example, referring briefly to FIG. 4, a top view of the first separator deck 110 of a separator in accordance with embodiments of the present disclosure is shown. The left side of FIG. 4 shows the separator deck 110, while the right side shows a cutaway view exposing the configuration of the probe 140 disposed below the separator deck 110. A screen (not shown) may be disposed across the separator deck 110. As shown in FIG. 4, probe 140 is disposed substantially perpendicular to a direction of fluid flow, indicated by arrow 4, along separator deck 110. Probe 140 is located about 75% of the length of the separator deck 110 from a feed end 114 of the separator deck 110. According to other embodiments the probe 140 may be located between approximately 50% and 95% of the length of the separator deck 110 from a feed end of the separator deck 110. According to some embodiments, two or more probes may be disposed beneath a separator deck 110.

For illustrative purposes, say the desired beach location is about 75% of the separator deck 110 from a feed end 114. Thus, the probe 140 as pictured in FIG. 4 is disposed at a desired beach location. As drilling fluid is provided to the vibratory separator 100 and the drilling fluid flows along separator deck 110, probe 140 may monitor a region or local volume proximate the probe 140 to determine the presence of liquid (i.e. drilling fluid). The probe may send a signal to an ECM or database. If the probe 140 detects fluid is present in the local volume, then a user or operator may determine that the beach is located between the desired beach location and the feed end 114. If the probe 140 determines fluid is not present in the local volume, then a user or operator may determine that the beach is located between the feed end 114 and the desired beach location. Based on the signal, the ECM or user may adjust operating conditions of the vibratory separator 100 to change the location of the beach. That is, if the beach is located between the desired beach location and the discharge end, the flow rate may be decreased, the angle of the separator deck 110 increased, the vibratory force may be increased, the motion profile changed, and/or the mesh size of the screen changed in order to shorten the length of the pool. If the beach is located between the feed end 114 and the desired beach location, then the flow rate may be increased, the angle of the separator deck 110 decreased, the vibratory force may be decreased, the motion profile changed, and/or the mesh size of the screen changed to move the beach closer to the desired beach location.

According to some embodiments, more than one probe 140 may be used to determine the location of the beach. For example, a first probe 140 may be disposed before a desired beach location (i.e. between the feed end 114 and the desired beach location), while a second probe 140 may be disposed after a desired beach location (i.e. between the desired beach location and a discharge end). Thus, the first and second probe may define a desired beach region. The first and second probe may send corresponding first and second signals to an ECM or database. Based on the signals, the ECM or user may determine a location of the beach and adjust the vibratory separator to change the location of the beach, as needed.

For example, if the first and second signals are different, then the beach is located in the desired beach region. As the beach is in the desired beach region, the user or operator may determine not to adjust the vibratory separator. If the first and second signals are the same, and fluid is not detected, then the beach may be located between the feed end 114 and the desired beach region and the user or operator may adjust operating conditions of the vibratory separator 100 to lengthen the pool (i.e. increase the flow rate, decrease the angle of the separator deck 110, decrease the vibratory force may be, change the motion profile, and/or change the mesh size of the screen). If the first and second signals are the same, and fluid is detected, the beach may be located between the desired beach region and the discharge end. Accordingly, the user or operator may adjust operating conditions of the vibratory separator 100 to shorten the pool (i.e. decrease the flow rate, increase the angle of the separator deck 110, increase the vibratory force may be, change the motion profile, and/or change the mesh size of the screen).

Additional examples of probe 140 configurations are discussed below. One skilled in the art will understand that the number of probes 140 and their position with respect to the separator deck 110 is not intended to limit the scope of the disclosure.

In a vibratory separator with multiple separator decks, at least one probe 140 may be disposed below one or more of the separator decks. For example, at least one probe 140 may be disposed beneath the first separator deck 110, at least one probe 140 may be disposed beneath the second separator deck 120, and at least one probe 140 may be disposed beneath the third separator deck 130. According to some embodiments, a plurality of probes may be disposed beneath the first and second separator decks 110, 120. As seen in FIG. 3, three probes 140 are disposed beneath each separator deck 110, 120, 130. The number of probes 140 disposed beneath each separator deck is not intended to be a limitation on the scope of the present disclosure. One having ordinary skill in the art will understand that any number of probes 140 may be disposed beneath each separator deck or a selected number of separator decks without departing from the scope of the present disclosure. For example, according to some embodiments, one probe 140, two probes 140, or more than three probes 140 may be disposed beneath one or more of the multiple separator decks.

Figure 6:
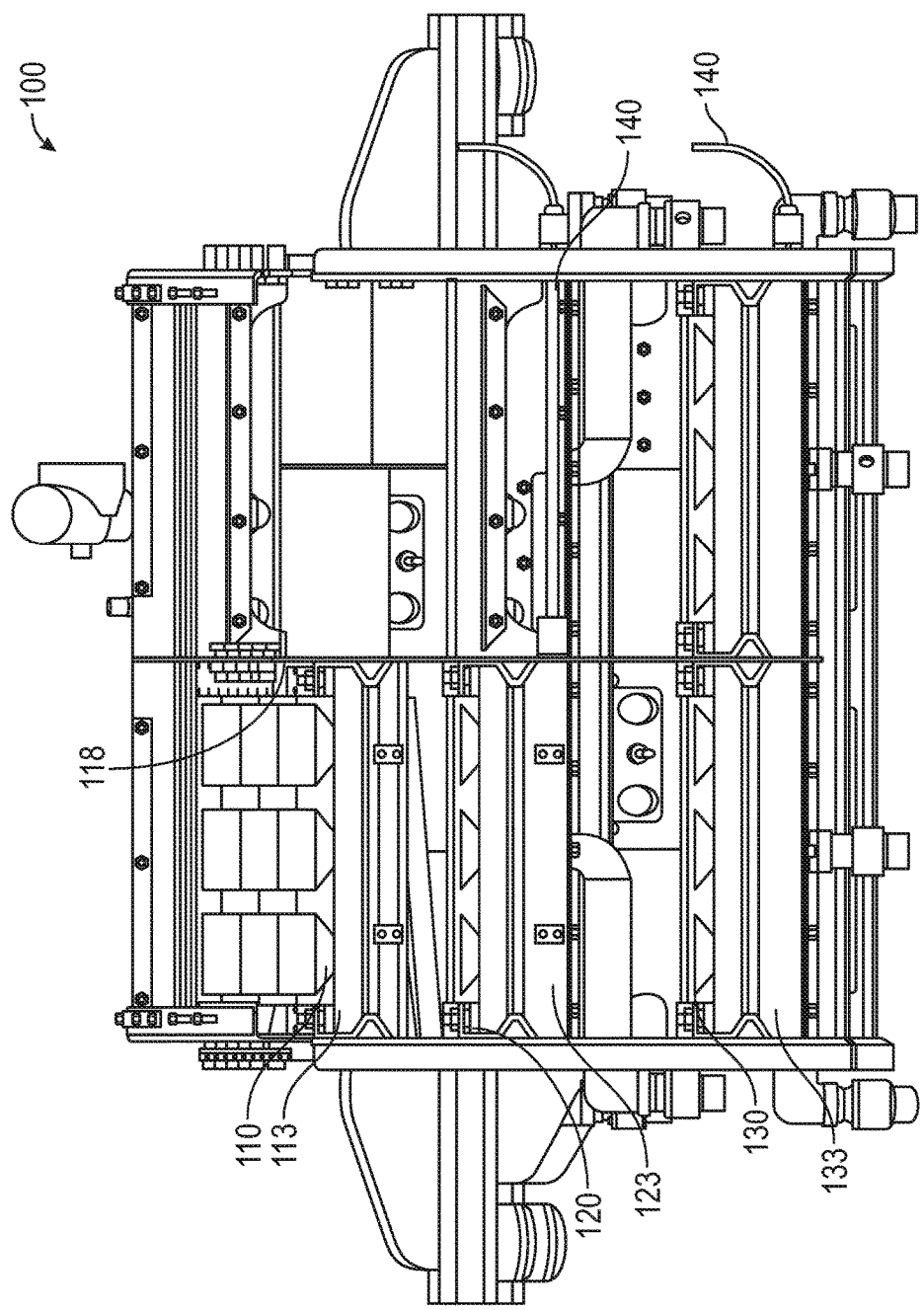
FIG. 6 shows a cross-sectional view of FIG. 5.
Figure 8:
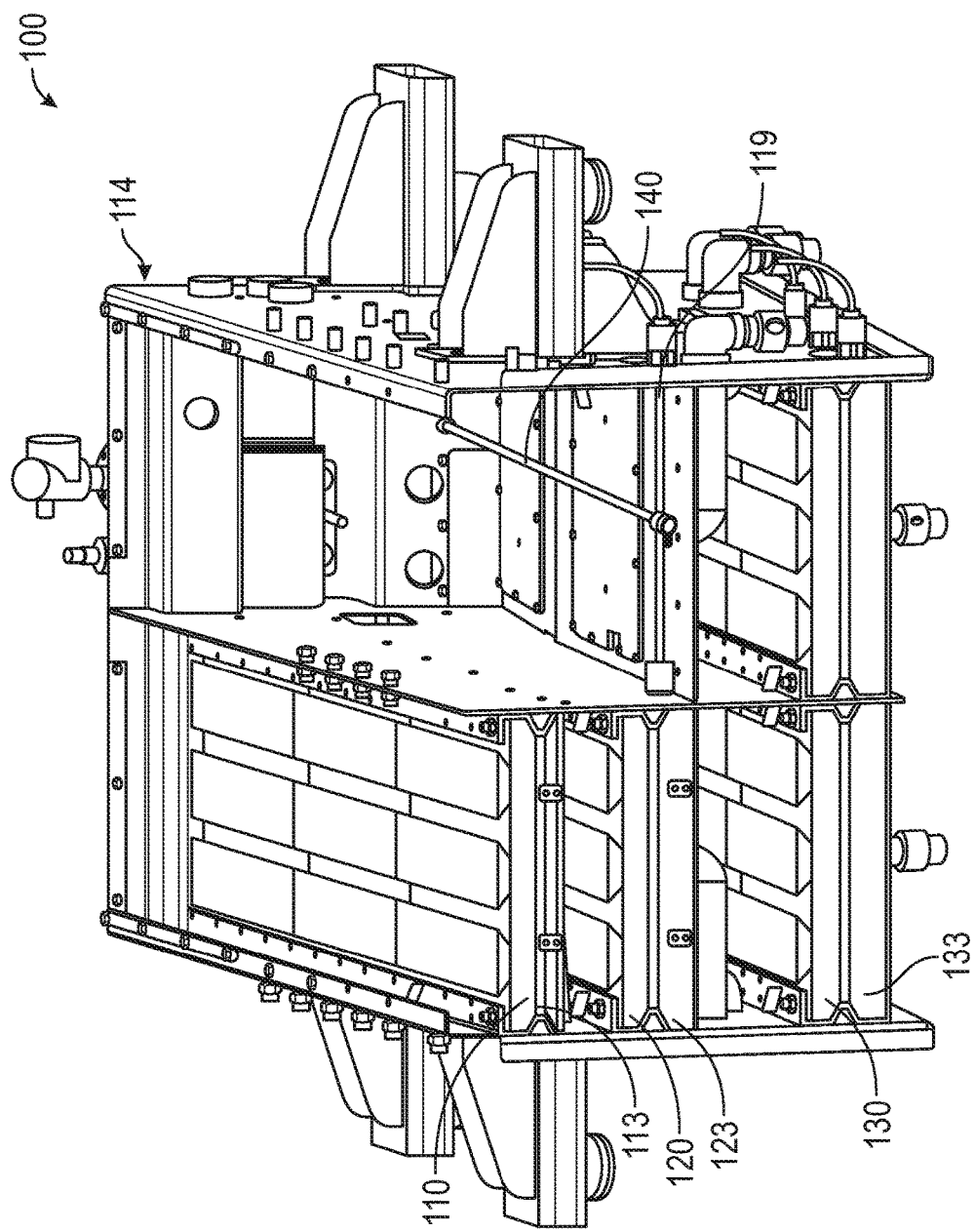
FIG. 8 shows a perspective view of FIG. 7.
Figure 10:
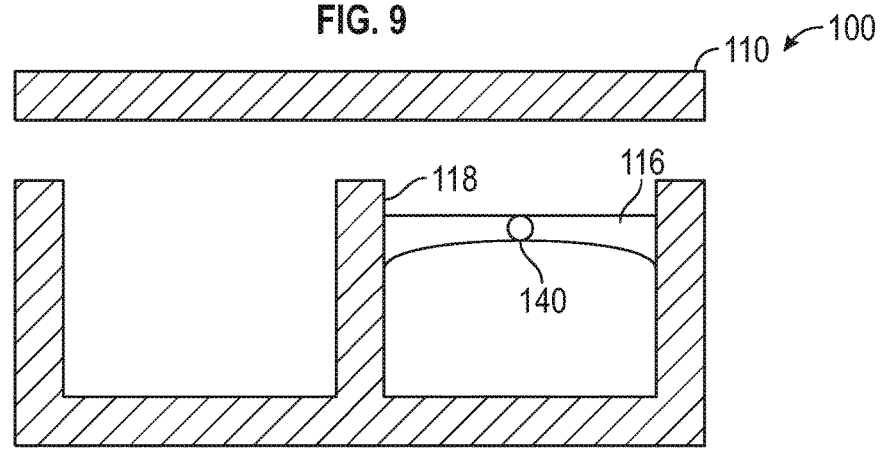
FIG. 10 shows a cross-sectional view of FIG. 9.

According to some embodiments, the probe 140 may be disposed between the separator deck 110 and a flow-back pan 113. As seen in FIG. 3, flow-back pan 113 may be disposed beneath separator deck 110 to collect the filtered fluid that passes through the screen of the separator deck 110. Referring now to FIGS. 6, 8, and 10, the flow-back pans 113, 123, and 133 may include a middle partition 118 to divide the flow of the filtered fluid into a left side and a right side. The partition 118 may be, for example, a vertically oriented plate or divider. The partition 118 may extend along a full length of flow-back pans 113, 123, and 133 or along a portion of flow-back pans 113, 123, and 133 and may be welded or secured in place with mechanical fasteners, for example, screws, rivets, or other fasteners known in the art. The middle partition 118 may allow fluid to be more evenly distributed in each of the flow-back pans 113, 123, and 133.

A separator deck may have a flow-back pan disposed beneath, such that a first separator deck has a first flow-back pan disposed beneath, a second separator deck has a second flow-back pan disposed beneath, and a third separator deck has a third flow back pan disposed beneath. In embodiments having multiple separator decks not every separator deck may have a flow-back pan. As pictured in FIG. 3, the flow-back pans may be included to distribute fluid between separator decks. For example, flow-back pan 113 may be configured to direct a first filtered fluid from the first separator deck 110 to the second separator deck 120. According to some embodiments, second flow-back pan 123 may direct a second filtered fluid from the second separator deck 120 to a third separator deck 130. According to some embodiments, a third flow-back pan 133 may provide the filtered fluid from the third separator deck 130 to a storage vessel or secondary separation device (not shown). According to some embodiments, the third separator deck 130 does not include a flow-back pan. Instead, the filtered fluid may be directly transferred to a storage vessel or secondary separation device for further processing.

According to some embodiments, the probe 140 may be disposed between each separator deck and flow-back pan. For example, at least one probe 140 may be disposed between the first separator deck 110 and the first flow-back pan 113, at least a middle probe 140 may be disposed between the second separator deck 120 and the second flow-back pan 123, and at least a lower probe 140 may be disposed between the third separator deck 130 and the third flow-back pan 133. According to embodiments where the third separator deck 130 may not have a corresponding flow-back pan, a probe 140 may be disposed beneath the third separator deck 130 and not in a corresponding flow-back pan. According to some embodiments, a plurality of probes 140 may be disposed between each separator deck and flow-back pan, as shown in FIG. 3. One of ordinary skill in the art will appreciate that various configurations of separator decks, probes, and flow-back pans may be used in accordance with embodiments disclosed herein and the scope of the application is not limited to any one configuration.

Still referring to FIG. 3, a reference probe 119 may be included in the separator 100. According to some embodiments, the reference probe 119 may be the same make and model as the probe 140. The reference probe 119 may be disposed proximate a feed end of the separator deck 110 perpendicular to a direction of fluid flow. According to some embodiments, the reference probe 119 may be disposed parallel or at an angle to the direction of fluid flow. According to some embodiments, the reference probe 119 may be disposed in a chamber at a feed end of the separator 100. According to some other embodiments, the reference probe 119 may be disposed in a mud box at the feed end of the separator 100. As one of ordinary skill in the art will recognize, the mud box may be a structure positioned on the separator above the feed end configured to receive and distribute fluid to the separator. The reference probe 119 may be shorter in length than probe 140. According to some embodiments, the reference probe 119 may be disposed beneath a single separator deck of a plurality of separator decks, for example, beneath separator deck 110. According to other embodiments, the reference probe 119 may be disposed beneath each separator deck, for example, beneath separator decks 110, 120, and 130. According to other embodiments, the reference probe 119 may be disposed above at least one separator deck. The reference probe 119 may be operatively coupled to an ECM. The reference probe 119 may be configured to send a reference signal to the ECM corresponding to a property of a local volume of the reference probe 119, wherein the reference prone 119 is coated in drilling fluid.

The reference signal from the reference probe 119 is indicative of a significant amount of fluid entering a local volume of probe 119 and being deposited on the reference probe 119. The reference probe 119 may be disposed at a feed end of the separator 100 where it may receive a stream of filtered fluid. A control signal or control value indicates when a probe 140 is exposed to air and/or no or minimal amounts of filtered fluid (in other words a minimal amount of fluid is entering the local volume of probe 140). A control value may be known for a given probe 140. For example, a control value may be about 0 pF for a probe 140 exposed to air. The reference signal and control value may be used to define bounds of exposure signal measured by the probe 140 at a given time, i.e. the probe 140 being coated in fluid and no fluid entering the local volume. As used herein, the term "reference signal" will refer to the signal from the reference probe 119 indicating a significant amount of fluid in the local volume and coating the reference probe 119 and the term "control value" will refer to a signal or value from the probe 140 corresponding to no or a minimal of fluid entering the local volume of probe 140. Thus, depending on the signals from the reference probe and the probe 140 an amount of fluid deposited on probe 140 may be determined.

According to some embodiments a control value may be determined. For example, the control value may be determined by recording a signal produced by the probe 140 when exposed only to air or minimal amounts of fluid. One having ordinary skill in the art will readily understand that due to the vibratory nature of the separator, even when the probe 140 is located between the beach and the discharge end of the vibratory separator, some amount of filtered fluid may be deposited on the probe 140. Thus, a control value of a probe 140 exposed only to air may serve as an approximation for a signal from the probe during operation. One having ordinary skill in the art will readily understand that determining a location of the beach may be performed without a reference signal or a control value.

Different fluids (e.g., muds) have different properties, e.g. dielectric constant and heat capacity, different fluids will produce different signals with probe 140 based on these properties. For example, a water based fluid may have a higher dielectric constant than an oil based mud. Thus, a signal from probe 140 corresponding to minimal amounts of a water-based fluid in the local volume may be similar to a signal from probe 140 corresponding to a substantial amount of oil-based fluid in the local volume. Therefore, determining a signal for a probe, i.e., a reference probe 119 fully coated in, for example, a drilling fluid, aids in accurately analyzing the signals from probe 140. Thus, the reference probe allows calibration of the incoming signal from probe 140 to be performed as the properties of the fluid, i.e. type of mud, changes during operation.

For example, a signal produced by the reference probe 119, may be used to determine other characteristics of fluid beyond the property i.e. capacitance or thermal conductivity, directly measured by the reference probe 119. If probe 119 and 140 are capacitance probes, the capacitance signal produced by the reference probe 119 may be used to determine if a fluid is oil-based or water-based. Determining the other characteristics of the fluid, e.g., if a fluid is oil-based or water-based may aid the user or operator in interpreting the signal from probe 140, as a water-based mud may have a different capacitance than an oil-based mud.

The probe 140 and the reference probe 119 may be mounted to a frame of the separator 100, a basket of the separator 102, the separator deck 110, 120, 130 or the flow-back pan 113, 123. The probe 140 and the reference probe 119 may be removably mounted within the separator 100 such that they may be removed and replaced if damage occurs during operation. The following description is provided with respect to probe 140, but one having ordinary skill in the art will understand that the reference probe 119 may be mounted in a similar manner. The probe 140 may be removably mounted within the separator 100 by any means known in the art. For example, a first end of the probe 140 may be threaded into a wall of the flow-back pan 113. A second end of the probe 140 may also be threaded into an opposite wall or middle partition 118 of the flow-back pan 113.

According to another embodiment, the second end of the probe 140 may be inserted into a receiving tube, cup or the like welded to the opposite wall of the flow-back pan 113, or middle partition 118. The cup may be lined with rubber to secure the second end of the probe 140 in place and dampen vibrations experience by probe 140. According to another embodiment, probe 140 may be mounted using Vanstone flanges at a first and second end of the probe 140 to secure the probe 140 to the flow-back pan 113. Although the above mounting methods have been described with respect to a flow-back pan 113, one having ordinary skill in the art will understand that a similar technique may be used to mount the probe 140 to a frame of the separator 100 and a basket 102 of the separator 100 without departing from the scope of the application.

According to another embodiment, a pair of brackets or flanges may be welded to a bottom of the separator deck 110 and a first end of the probe 140 may be attached to a first bracket and a second end of the probe 140 may be attached to a second bracket. The first and second ends of the probe 140 may be attached to the brackets using the above described attachment mechanisms, for example, threads, Vanstone flanges, and a thread and rubber-cup configuration.

Referring to FIGS. 5-11, additional configurations of the probe 140 are shown. Although the following embodiments are shown with respect to separator deck 110, one having ordinary skill in the art will readily understand that the configurations shown in FIGS. 4-11 may be used in any combination for the second or subsequent separator decks e.g. separator decks 120 and 130. Further, although the embodiments shown in FIGS. 8, 10, and 12 include a flow back pan 113, one having ordinary skill in the art will readily understand that similar configurations may be implemented without a flow-back pan 113. For example, the probe 140 may be mounted to a wall of a basket 102, the separator deck 110, or the separator 100.

Figure 5:
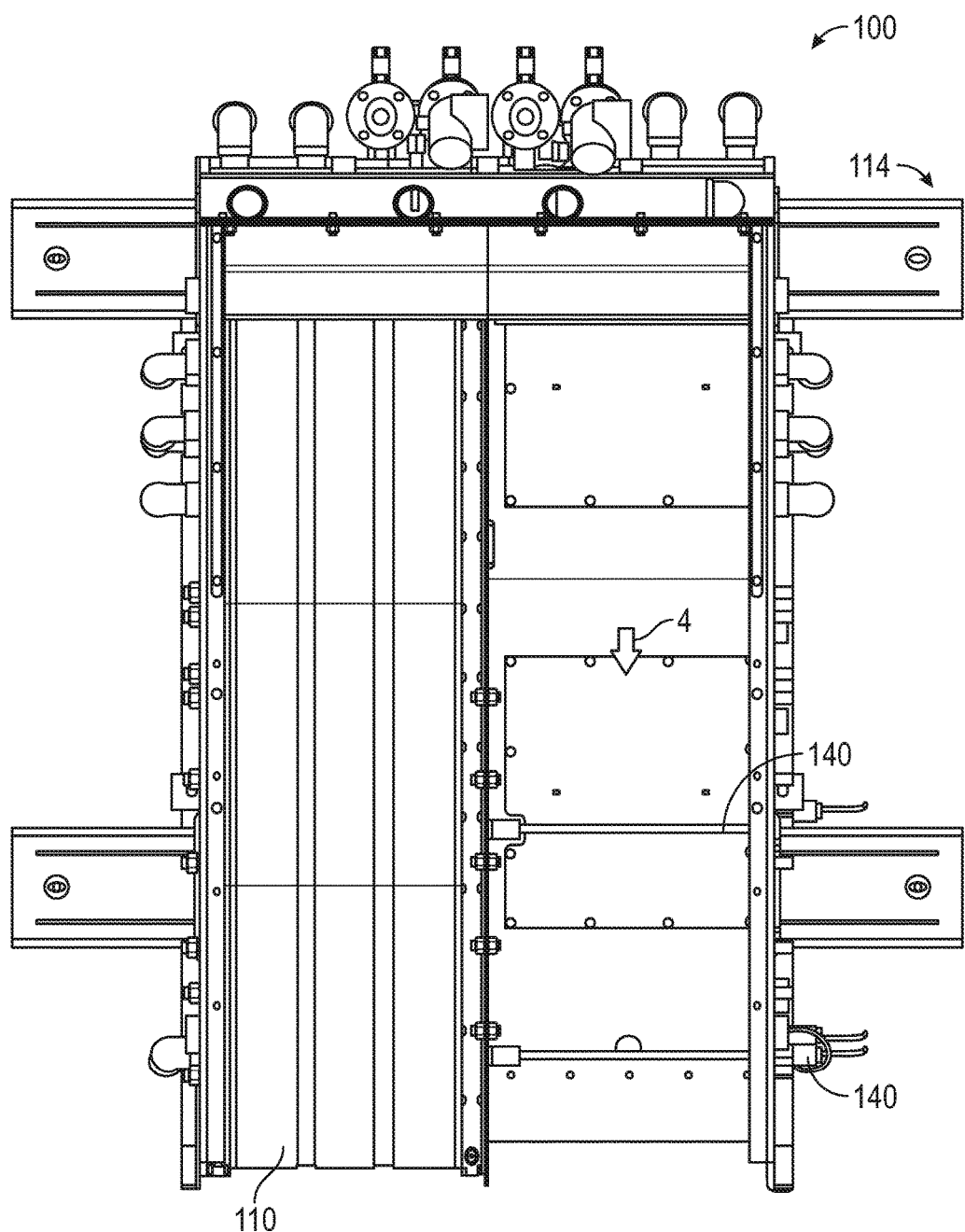
FIG. 5 shows a top view of a separator in accordance with embodiments of the present disclosure.

FIG. 5 shows a top view of the first separator deck 110 of a separator in accordance with embodiments of the present disclosure. The left side of FIG. 5 shows the separator deck 110, while the right side shows a cutaway view exposing the configuration of probes 140 disposed below the separator deck 110. A screen (not shown) may be disposed on the separator deck 110. The reference probe (not shown) may be disposed near a feed end 114 of the separator. Similar to FIG. 4, the probes 140 are disposed substantially perpendicular to a direction, indicated by arrow 4, of fluid flow along the separator deck 110. Two probes 140 are disposed proximate a desired beach location, such that a first probe 140 is disposed a distance from the feed end 114 less than a desired beach location and a second probe is disposed a distance from the feed end 114 greater than a desired beach location. For example, if a desired beach location is 75% of the length of the separator deck from a feed end 114, the first probe 140 may be disposed at a position corresponding to 70% of the length of the separator deck 110 from the feed end 114 and the second probe may be disposed at a position corresponding to 80% of the length of the separator deck 110 from a feed end. In other embodiments, the first probe 140 may be disposed at a position approximately 65% of the length of the separator deck 110 from the feed end 114 and the second probe may be disposed at a position corresponding to 85% of the length of the separator deck 110 from the feed end 114. One having ordinary skill in the art will understand that any number of probes 140 may be disposed proximate a desired beach location and at various distances from the desired beach location without departing from the scope of the present disclosure.

Figure 7:
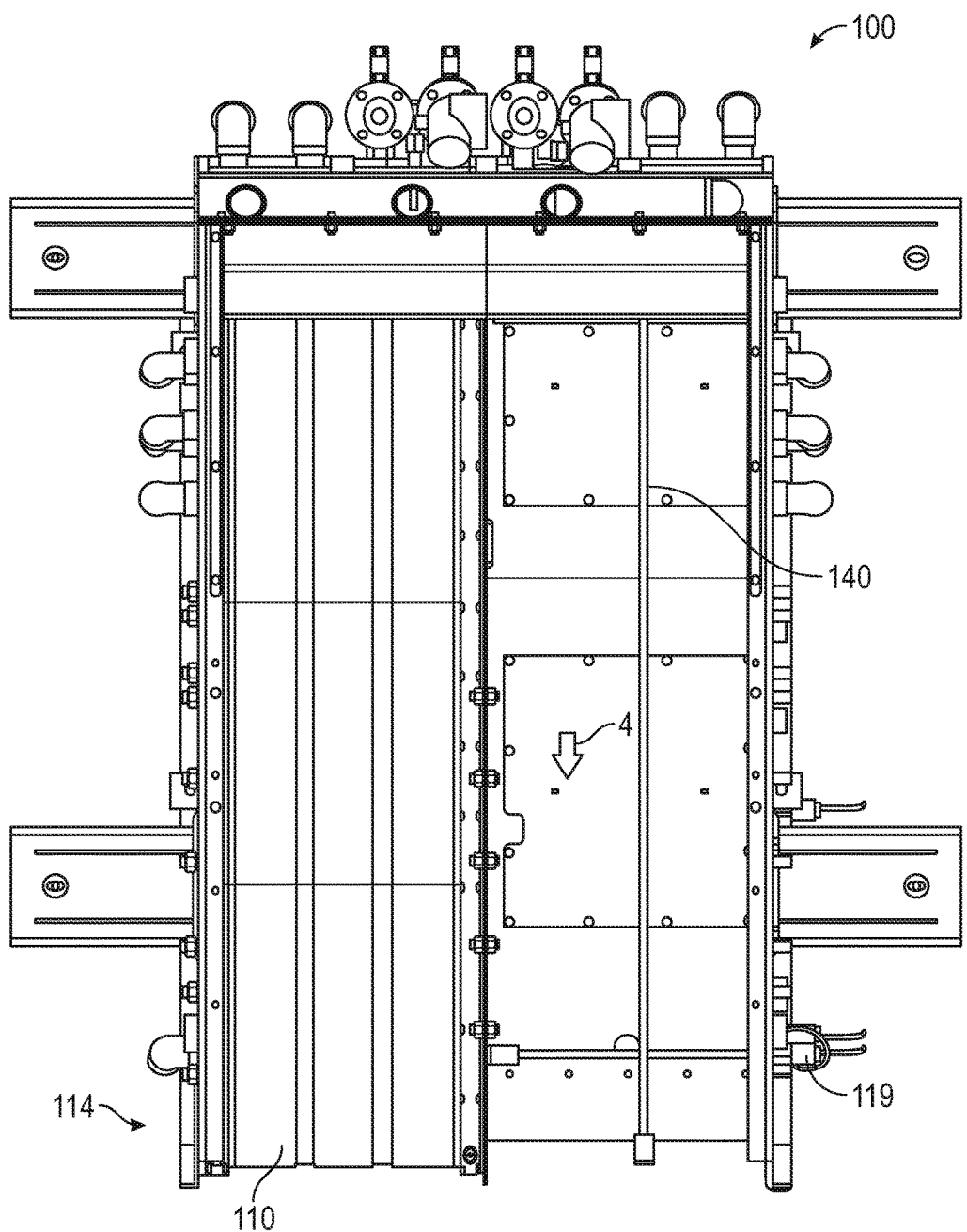
FIG. 7 shows a top view of a separator deck in accordance with embodiments of the present disclosure.
Figure 9:
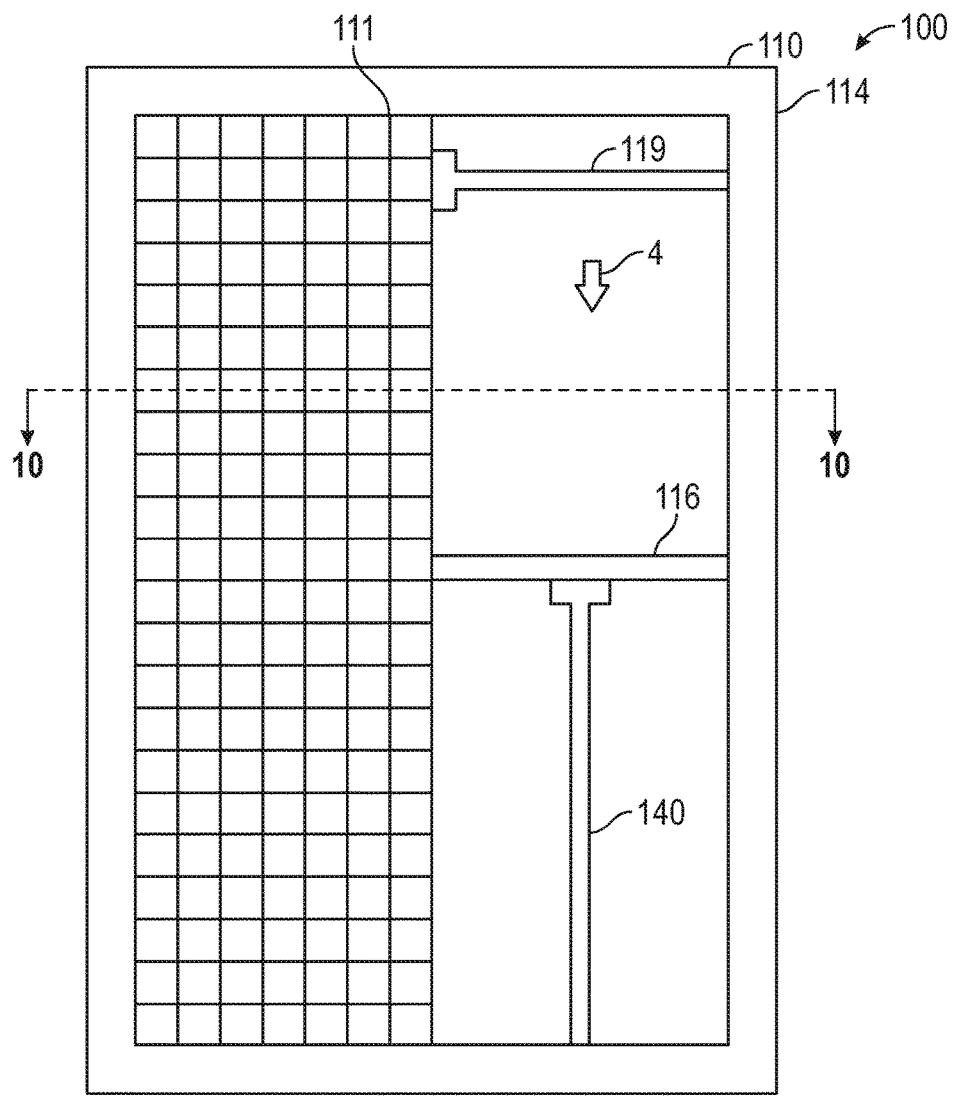
FIG. 9 shows a top view of a separator deck in accordance with embodiments of the present disclosure.

FIGS. 7 and 9 show top views of the first separator deck 110 of a separator according to embodiments of the present disclosure. Arrows 4 indicate a direction of flow along the separator deck 110. A reference probe (not shown) may be disposed near a feed end 114 of the separator. A probe 140 may be disposed substantially parallel to a direction of fluid flow. As seen in FIG. 7, the probe 140 may span an entire length or substantially the entire length of the separator deck 110. A first end of the probe may be mounted to a wall of the flow-back pan, basket, or separator near a feed end; while a second end of the probe 140 may be mounted to a wall of the flow-back pan, basket, or separator near a discharge end.

As seen in FIG. 9, the probe 140 parallel to the direction of flow along the separator deck 1100 may span a portion of the length of the separator deck 110 near a desired beach location; that is, the probe 140 is disposed such that it intersects a boundary corresponding to the desired beach location. According to this embodiment, a support wall 116 may be welded or mounted (e.g., by mechanical fasteners, adhesives, etc.) to a flow back pan, a basket, the separator deck, or the separator, below the separator deck 110 to receive a first end of the probe 140. Referring to FIG. 10, the support wall 116 may be configured such that it does not substantially interfere with the flow of filtered fluid. A second end of the probe 140 may be mounted to a wall of the flow-back pan 113, basket 102, the separator deck 110 or separator 100 near a discharge end. According to some embodiments, more than two probes 140 may be disposed parallel to a direction of fluid flow without departing from the scope of the present disclosure.

Figure 11:
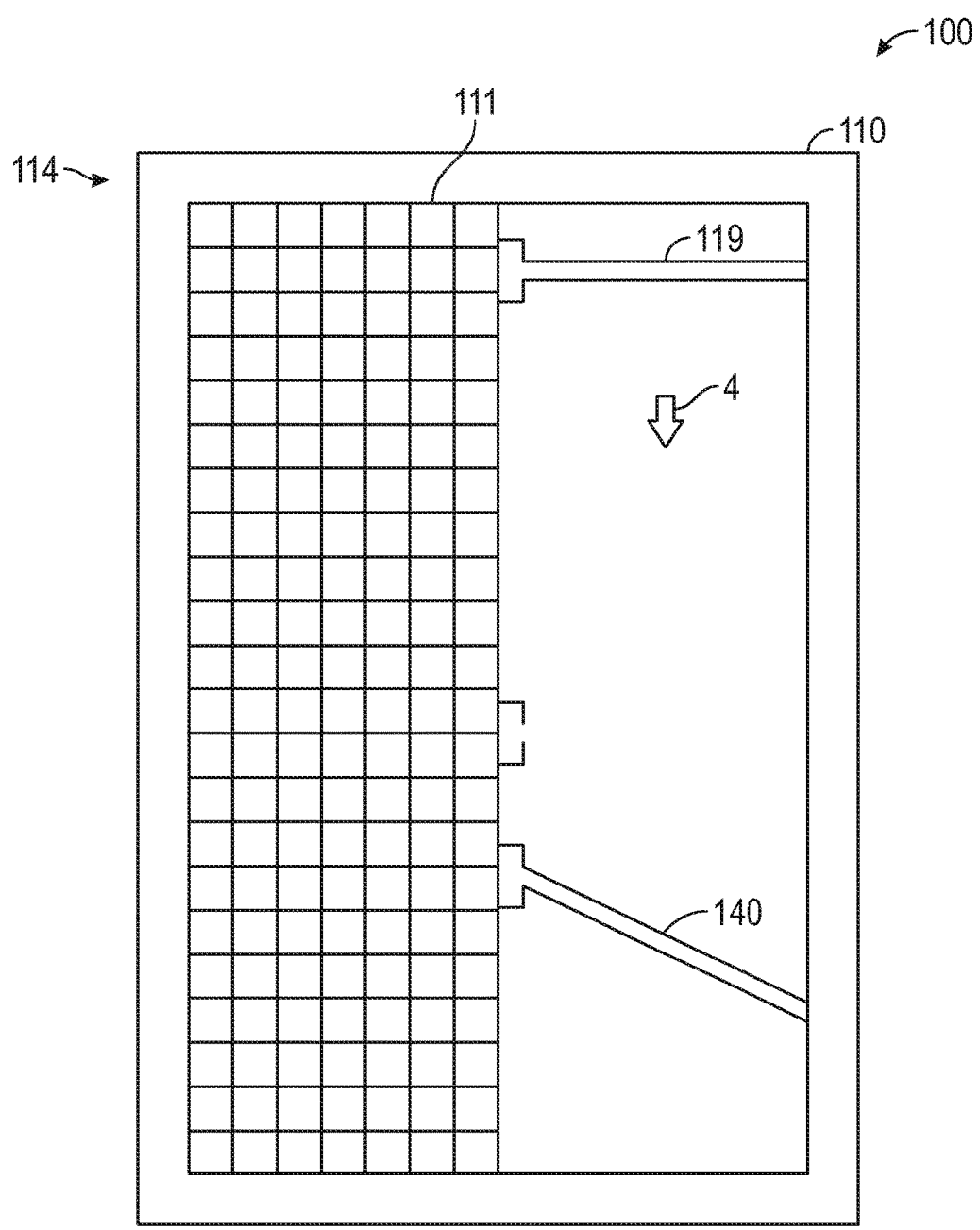
FIG. 11 shows a top view of a separator deck in accordance with embodiments of the present disclosure.

FIG. 11 shows a top view of the separator deck 110 of a separator according to embodiments of the present disclosure. Arrow 4 indicates a direction of flow across separator deck 110. FIG. 11 shows probe 140. A reference probe 119 may be disposed at the feed end 114 of the separator 100. The probe 140 is disposed at an angle with respect to a direction of fluid flow along separator deck 110. For example, the probe 140 may be disposed at an angle of about 45° with respect to the direction of fluid flow across separator deck 110. According to some embodiments, the probe 140 may be disposed at an angle of about 30° to 60°. The probe 140 may be disposed proximate a desired beach location. The probe 140 may intersect a line about perpendicular to the direction of fluid flow along the deck corresponding to the desired beach location. For example, if a desired beach location is about 75% the length of the separator deck from a feed end 114, the probe 140 may intersect a line corresponding to a distance about 75% the length of the separator deck 110.

Figure 12:
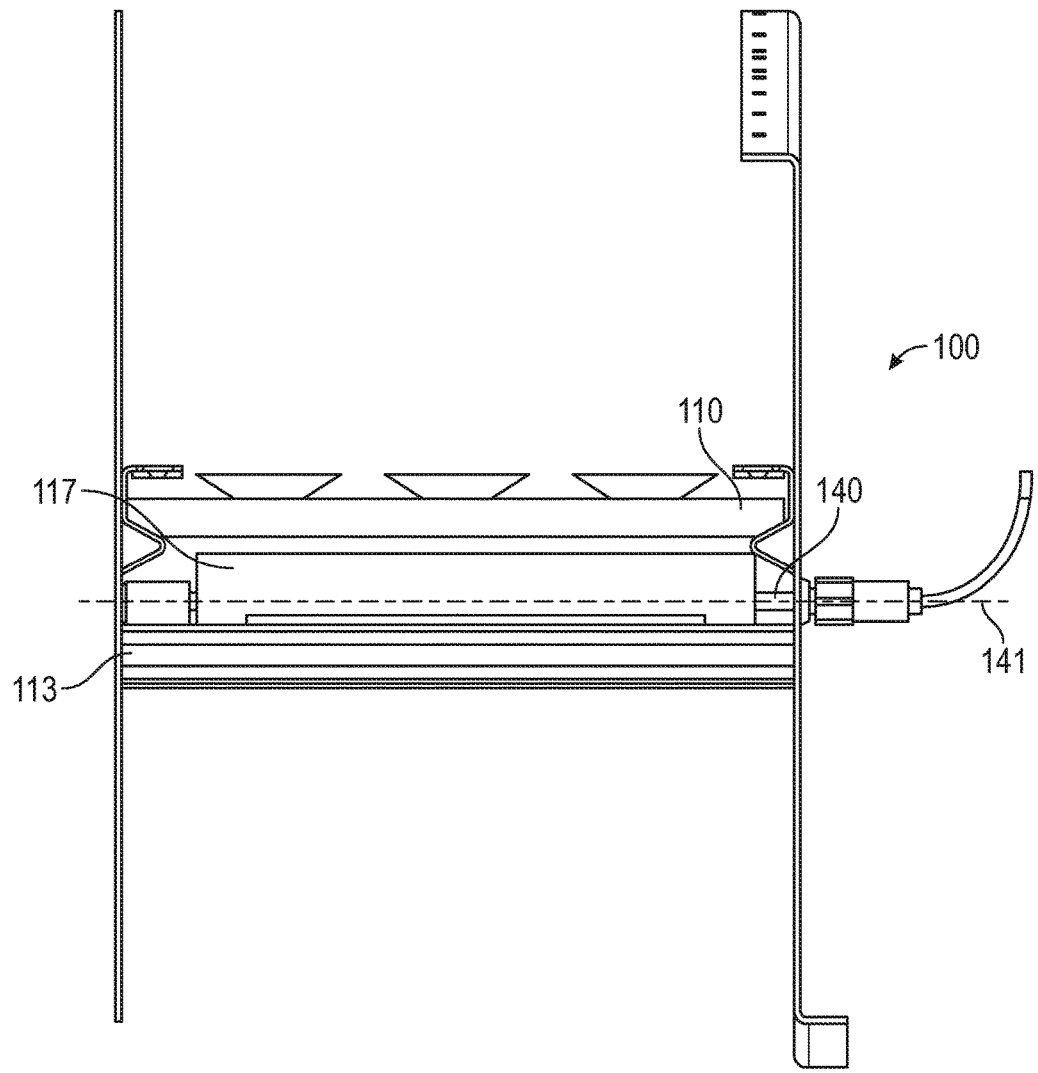
FIGS. 12 and 13 show cross-sectional views of a flow-back pan in accordance with embodiments of the present disclosure.

Referring to FIGS. 12 and 13, embodiments of the present disclosure may also include a gutter or channel 117 disposed proximate the probe 140 or the reference probe to funnel or direct filtered fluid from the separator deck 110 to the probe 140. The channel 117 is provided in the separator 100 to collect the filtered fluid as it passes through the screen (not shown) of separator deck 110 to provide a concentrated collection of the filtered fluid to a local volume of the probe 140 for measurement. The channel 117 may have a cross-section that is v-shaped, rectangular, trapezoidal, hemispherical, or any other channel shape known in the art for collecting fluid. The channel 117 may be provided with a series of apertures or holes in either the sidewalls, bottom portion, or a combination of sidewalls and the bottom portion to allow fluid to collect in the channel 117 and exit the channel 117. The apertures may be sized such that any particulate matter that passes through the first separator deck 110 will also pass through the channel 117 and not clog the apertures. The channel 117 may be welded to the walls of the flow-back pan 113. One having ordinary skill in the art will understand that the channel 117 may also be mechanically fastened to the walls of the flow back pan 113, with screws, rivets, and other mechanical fasteners known in the art. According to some embodiments, the channel 117 may be welded or mechanically fastened to a basket 102 of the separator 100, the separator deck 110, or walls of the separator 100.

The channel 117 may be disposed either above or below the probe 140 or the reference probe 119. Referring to FIG. 12, channel 117 is disposed beneath the probe 140. According to this embodiment, the probe 140 is disposed within the channel 117, thereby ensuring fluid from the separator deck 110 is directed to the local volume and deposited on the probe 140. By collecting the filtered fluid in the channel 117, the amount of fluid entering the local volume and contacting probe 140 may also be more concentrated. In other words, the channel directly funnels or captures fluid filtered by the separator deck 110 to enter the local volume and be sensed by probe 140, thereby enhancing the signal produced by the probe 140. In other words, the signal of the probe 140 may be amplified and less noisy. Referring to FIG. 13, channel 117 may be disposed above the probe 140. As seen in FIG. 13, the channel 117 may collect the filtered fluid as the fluid passes through the separator deck 110. The collected fluid in the channel 117 may exit the channel 117 through the apertures and be deposited onto the probe 140 disposed below. Thus, probe 140 receives a steadier and focused stream of filtered fluid.

The probe 140 may operate by measuring a property of a local volume. The probe 140 generates a signal based on the measured property of local volume. The signal may be sent from the probe 140 to an electronic control module (ECM) and/or a database. Next a location of a beach on the separator deck may be determined based on the signal. According to some embodiments the ECM may automatically determine a location of the beach or a user may read the signal sent to the ECM and determine a location of the beach. Once a location of the beach has been determined the separator 100 may be adjusted to maintain a desired position of the beach. For example, if the beach is not in a desired position on the separator deck 110 (e.g., if the beach is too close to the feed end or the discharge end of the separator) a flow rate of fluid to the separator 100, an angle of the first separator deck 110, an angle of the separator 100, or an angle of a basket 102 of the separator 100 may be adjusted to change a desired position of the beach. If the beach is near a desired beach location, then the ECM or operator may maintain current separatory conditions.

According to some embodiments, the method may include depositing a fluid on the first separator deck 110 disposed in a vibratory separator 100. As the fluid flows onto and along the length of the first separator deck 100, the drilling fluid may be separated into a first filtered fluid component and a first solids component with a screen disposed in the separator deck. One having ordinary skill in the art will understand that monitoring a location of the beach may be performed continuously during the separation process so that the beach can be maintained in the desired location for more efficient separation of the solids from the fluid. According to other embodiments, the ECM or user may periodically check the location of the beach and adjust various parameters of the separator accordingly, e.g. angle of the separator deck, flow rate, etc.

With reference to FIG. 4, as fluid is fed to the separator and deposited on a feed end of separator deck 110, a beach may form on the separator deck 110. If the length of a pool is shorter than the distance of probe 140 from a feed end 114 of the separator deck 110, then filtered fluid passing through the separator deck 110 may not enter the local volume of probe 140 and/or be deposited on probe 140. Throughout operation or periodically, the probe 140 may send a corresponding signal to an electronic control module (ECM) and/or a database. In response, the ECM may send instructions to the separator to adjust a separator parameter (e.g., the angle of the deck, basket, or separator) or instructions to increase the flow rate to the separator (e.g. instructions sent to a valve upstream of the separator). Such adjustment to the separator 100 or fluid flow rate may thereby lengthen the pool bringing the beach location closer to probe 140. The probe may continuously or periodically monitor or measure the local area filtered fluid through the separator deck 110 to determine if the beach is located proximate the probe or in a desired position.

According to some embodiments, a second probe may be disposed beneath the separator deck 110. The second probe may send a second signal to the ECM. The ECM or a user may compare the signals from the first and second probes 140 to determine a location of the beach. For example, if the signals from the first and second probes 140 are similar to a control value, then the ECM may determine that a length of the pool is less than a desired beach. The separator 100 or flow rate may then be adjusted to lengthen the pool (e.g., increasing fluid flow to the separator 100, decreasing an incline angle of a separator deck 110, increasing the vibratory force, changing the motion profile, and changing the mesh size of the screen). If the signal from the first probe 140 is different from the second signal from the second probe 140, then the beach may be located between the first and second probes 140, proximate a desired beach location. If the signals from the first and second probes 140 are not similar to the control value, then the length of the pool may be greater than the position of the second probe 140 and the separator 100 or flow rate may then be adjusted (e.g., reducing fluid flow to the separator 100 or increasing an incline angle of a separator deck 110) to shorten the pool. One having ordinary skill in the art will understand that determining a location of the beach may be performed without a control value, for example, by comparing the first and second signals to each other.

One having ordinary skill in the art will understand that according to some embodiments, the determination to adjust a separator parameter or fluid flow rate to lengthen the pool may be made automatically by the ECM as well as by a user controlling the ECM. If the length of the pool is greater than or about equal to the distance of probe 140 from a feed end of the separator deck 110, then probe 140 may receive a steady deposit of filtered drilling fluid. The probe 140 may send a corresponding signal to the ECM. The ECM or a user may then determine whether to maintain current separator conditions, i.e. flow rate, angle of the separator deck 110, and/or angle of the basket 102, etc.

The measurement obtained by the probe 140 and corresponding signal may be, for example, a capacitance value of a fluid taken by a capacitance probe, a thermal conductivity value of a fluid taken by a thermal diffusivity probe, or any other property and corresponding probe known in the art. The corresponding signal may be an analog signal that indicates, for example, the capacitance measured by the probe 140 based on the amount of fluid deposited on the probe 140. The capacitance signal may be compared to a reference signal and/or control value to determine the amount of fluid deposited on the probe 140. In other embodiments, the corresponding signal may indicate a thermal conductivity of the local volume. Depending on the configuration of the probes, the signal sent by probe 140 may indicate how much fluid is present, if any, at a certain location along the length of the separator deck 110.

According to some embodiments, a reference probe 119 may be disposed proximate a feed end of the first separator deck 110 to measure a property of a local volume proximate a probe. The reference probe 119 may be a similar make and model to the measurement probe 140. The reference probe 119 may be smaller than the first probe 140 and may be disposed in a feed end chamber of the separator 100. A second signal may be sent from the reference probe 119 to the ECM. The second signal from the reference probe 119 may be used to determine a relative strength of a first signal from probe 140.

For example, a reference probe 119 may be disposed at a feed end 114 of a separator deck 110 having a probe configuration shown in FIG. 4. The reference probe 119 may be disposed in a location where the reference probe 119 may be exposed to the feed fluid entering the separator deck or may be submerged in the feed fluid. As the fluid to be separated is deposited at the feed end of a separator 100, a pool may form on the first separator deck 110. As filtered fluid from the pool passes through the first separator deck 110, the reference probe 119 may receive a stream of fluid, thereby coating the reference probe 119 with fluid. Additionally, fluid may enter the local volume of probe 140. The reference signal from the reference probe 119 may be compared to the signal from probe 140. Thus, the reference probe 119 provides a reference signal, i.e. an example of a signal from the probe 140 if fully coated or in substantial contact with the wellbore fluid. By comparing the reference signal to the signal from probe 140, an operator may determine if fluid is entering the local volume of the probe 140 and being deposited on the probe 140, much like a digital (on/off) signal. For example, if the signal from probe 140 is similar to the reference signal, then the pool may be located above the probe 140. If the signal from probe 140 is similar to the control value (i.e., signal from probe 140 indicating the probe 140 is exposed to air and/or no or minimal amounts of filtered fluid), then the beach may be not be located above the probe, and the pool does not extend past the location of the probe 140. Thus, the operator may determine a location of the beach and/or a subsequent action to adjust the location of the beach. One having ordinary skill in the art will readily understand that determining a location of the beach may be performed without a control value. For example, if the signal from probe 140 is significantly less than the reference signal, then it may be determined that no fluid or minimal amounts of fluid are entering the local volume.

According to some embodiments, the signal from the reference probe 119 may be compared to the signal from the probe 140 to determine the presence of fluid within the local volume at a given time, much like an analog signal. In other words, the signal from the probe 140 may have a value between the reference signal and the control value. For example, referring to FIGS. 7 and 9, filtered fluid passing through the separator deck 110 and falling on probe 140 will produce a measurement (signal) that is sent to the ECM. The reference probe 119 will similarly produce a reference signal that is sent to the ECM. While the signals from probes 140 in FIGS. 4 and 5 (i.e., where the probes are positioned perpendicular to the direction of fluid flow along the separator deck) are analyzed to determine if fluid flow (e.g., a significant amount) is being deposited on said probes 140, the signal from probes in embodiments of FIGS. 7 and 9 (i.e., where the probes are positioned parallel to the direction of fluid flow along the separator deck) may be analyzed to determine how much of the probe 140 is exposed to a steady stream of filtered fluid. Because the signal from probe 140 is analog, the amplitude of the signal from the probe 140 may be proportional to the amount of fluid deposited along the length of the probe 140. For example, if the pool length covers 50% of the length of the probe 140, the resulting signal may be about half of the value of the reference signal.

Based on the desired beach location and position of probe 140 with respect to the desired beach location, a range of acceptable signal values for probe 140 may be determined. For example, referring to FIG. 7, if the desired beach location is 75% from a feed end 114 of the separator deck 110, because probe 140 spans the length of the deck, a range of acceptable signal values may be 75%±5% of the reference signal. That is for a range of about 70% to 80% of a reference signal, the beach is near the desired beach location. If the signal from probe 140 is greater than the acceptable range, the separator 100 or flow rate may then be adjusted (e.g., the flow rate may be decreased, the angle of the separator deck 110 increased, the vibratory force may be increased, the motion profile changed, and/or the mesh size of the screen changed) to shorten the pool. If the signal from probe 140 is less than the acceptable range, the separator or flow rate may then be adjusted (e.g. the flow rate may be increased, the angle of the separator deck 110 decreased, the vibratory force decreased, the motion profile changed, and/or the mesh size of the screen changed) to lengthen the pool. One having ordinary skill in the art will understand that the size of the acceptable range may vary according to various filtering conditions and applications. For example, the acceptable range may be a range of about 5%, 10%, or 20%.

The signal from probe 140 of FIG. 11 may be processed similarly to the above description with respect to the probes 140 in FIGS. 7 and 9. That is, based on the desired beach location and position of probe 140 with respect to the desired beach location, a range of acceptable signal values for probe 140 may be determined. For example, referring to FIG. 11, if the desired beach location is 75% from a feed end of the separator deck 110, because the midpoint of probe 140 is about 75% from a feed end of the separator deck, a range of acceptable signal values may be 50%±5% of the reference signal. That is for a range of about 45% to 55% of a reference signal, the beach is near the desired beach location. If the signal from probe 140 is greater than the acceptable range, the separator or flow rate may then be adjusted (e.g., the flow rate may be decreased, the angle of the separator deck 110 increased, the vibratory force may be increased, the motion profile changed, and/or the mesh size of the screen changed) to shorten the pool. If the signal from probe 140 is less than the acceptable range, the separator or flow rate may then be adjusted (e.g. the flow rate may be increased or the angle of the separator deck 110 decreased, the vibratory force decreased, the motion profile changed, and/or the mesh size of the screen changed) to lengthen the pool.

Referring back to FIG. 5, according to some embodiments, a first probe 140 and a second probe 140 may be included to measure a position of the beach. The second probe 140 may send a third signal to the ECM and/or database. The first and third signals from the first and second probes may then be compared to the second signal from the reference probe to determine a location of the beach, as described below. According to some embodiments the third signal and the second signal may be compared to each other without a reference probe to determine a location of the beach.

As fluid is fed to the separator 100 and deposited on a feed end 114 of separator deck 110, a beach may form on the separator deck 110. Filtered fluid passing through the separator deck 110 entering the local volume and being deposited on the reference probe 119 will produce a reference signal that is sent to an ECM. Signals from the first and second probes 140 may also be sent to the ECM. The ECM or a user may compare the reference signal from the reference probe to the signals from the first and second probes 140 to determine a location of the beach. For example, if the signals from the first and second probes 140 are similar to a control value, then the ECM may determine that a length of the pool is less than a desired beach. The separator or flow rate may then be adjusted to lengthen the pool (e.g., increasing fluid flow to the separator or decreasing an incline angle of a separator deck 110). If the signal from the first probe 140 is similar to the reference signal, while the signal from the second probe 140 is similar to a control value, then the beach may be located between the first and second probes 140, proximate a desired beach location. If the signals from the first and second probes are similar to the reference signal, then the length of the pool is greater than the position of the second probe 140 and the separator or flow rate may then be adjusted (e.g., reducing fluid flow to the separator or increasing an incline angle of a separator deck) to shorten the pool. One skilled in the art will understand that using more than one probe 140 to determine a location of the beach may be performed without a reference probe or control value.

Referring to FIG. 3, according to some embodiments, after fluid passes through the first separator deck 110, the first filtered fluid may be collected in a first flow-back pan 113. The first flow-back pan 113 may then direct the first filtered fluid to a second separator deck 120. The second separator deck will then separate the first filtered fluid into a second filtered fluid component and a second solid component. A third probe 140 disposed beneath the second separator deck 120 may measure a position of a second beach by measuring a fluid property of the second filtered fluid deposited thereon. The third probe 140 may then send a fourth signal to the ECM and a separator parameter, e.g. a flow rate or angle of inclination of the second separator deck 120 may be adjusted based on the fourth signal. According to some embodiments, the separator 100 may include a fourth probe 140 disposed beneath the second separator deck 120, such that the third probe 140 and the fourth probe 140 may determine a location of the second beach.

According to some embodiments, each probe including the reference probe 119 may have a channel 117 disposed proximate the probe. According to some embodiments, the probe may be disposed with in the channel 117 such that the probe detects a property of the fluid within the channel 117. The first filtered fluid may then exit the channel 117 through at least one aperture disposed in the channel 117 to a flow-back pan disposed beneath the probe or to another separator deck. According to other embodiments, the channel 117 may be disposed above the probe such that the first filtered fluid exiting the apertures are deposited on the probe. One having ordinary skill in the art will understand that any number of probes may have a channel 117, while the remaining probes may not have a channel 117.

Although the preceding description has been described herein with reference to particular means, materials and embodiments, it is not intended to be limited to the particulars disclosed herein. Rather, it extends to all functionally equivalent structures, methods and uses, such as are within the scope of the appended claims.

The invention claimed is:

1. An apparatus comprising:
   a separator deck capable of separating solids from a liquid-solid mixture;
   a first probe disposed beneath the separator deck to determine a position of a beach between the liquid-solid mixture and separated solids.

2. The apparatus of claim 1, wherein the first probe is disposed proximate a desired beach location on the separator deck.

3. The apparatus of claim 1, further comprising a second probe disposed beneath the separator deck, such that a position along the length of the separator deck corresponding to a desired beach location is located between the first and second probe.

4. The apparatus of claim 1, further comprising a reference probe disposed proximate a feed end of the separator deck.

5. The apparatus of claim 1, further comprising a channel disposed above the first probe between the separator deck and the first probe.

6. The apparatus of claim 1, further comprising a channel, the first probe being disposed in the channel.

7. A method comprising:
   measuring a property of a local volume of liquid with a first probe disposed beneath a first separator deck;
   sending a first signal from the first probe to a database; and
   determining a location of a beach based on the first signal.

8. The method of claim 7, further comprising adjusting at least one of a flow rate or an angle of the first separator deck based on the first signal to maintain a desired position of the beach.

9. The method of claim 7, wherein the measuring comprises measuring a capacitance detected by the first probe, wherein the first probe is a capacitance probe.

10. The method of claim 7, wherein the measuring comprises measuring a thermal conductivity of the local volume, wherein the first probe is a thermal diffusivity probe.

11. The method of claim 7, further comprising collecting a first filtered drilling fluid in a channel disposed beneath the first probe or above the first probe, wherein the first probe detects a property of the first filtered drilling fluid in the channel; and
flowing the first filtered drilling fluid from at least one aperture disposed in the channel to a flow pan disposed beneath the first probe.

12. The method of claim 7, further comprising:
measuring a property of a first filtered fluid with a reference probe disposed proximate a feed end of the first separator deck;
sending a second signal from the reference probe to the database; and
comparing the first signal from the first probe to the second signal from the reference probe to determine an adjustment to at least one of a flow rate and an angle of the first separator deck.

13. The method of claim 7, wherein determining the location of the beach further includes measuring a property of a first filtered fluid with a second probe disposed between the first probe and a discharge end of the first separator deck.

14. The method of claim 13, further comprising:
sending a third signal from the second probe to the database; and
comparing the third signal from the second probe to the first signal from the first probe to determine the location of the beach.

15. The method of claim 7, further comprising:
depositing a fluid on the first separator deck, wherein the first separator deck is disposed in a vibratory separator;
forming the beach on the first separator deck; and
separating the fluid into a first filtered fluid component and a first solid component with the first separator deck.

16. The method of claim 7, further comprising:
collecting the first filtered fluid in a first flow-back pan;
directing the first filtered fluid to a second separator deck;
separating the first filtered fluid into a second filtered fluid and a second solids component with a second screen disposed in the second separator deck;
measuring a position of a second beach by depositing the second filtered fluid onto a third probe disposed beneath the second separator deck;
sending a fourth signal from the third probe to the database; and
adjusting at least one selected from a flow rate and an angle of the second separator deck based on the fourth signal.

17. A method comprising:
monitoring a region proximate at least one probe to determine a presence of a liquid, wherein the at least one probe is disposed beneath a first separator deck of a vibratory separator;
sending a signal from the probe to a database;
determining a location of a beach of the separator deck based on the presence of the liquid; and
at least one of adjusting or maintaining operating conditions of the vibratory separator based on the location of the beach.

18. The method of claim 17, wherein the beach is located in a desired beach region further comprising maintaining the conditions of the vibratory separator.

19. The method of claim 17, wherein the beach is located between a feed end of the separator deck and a desired beach region further comprising adjusting the conditions of the vibratory separator to move the beach closer to the desired beach region.

20. The method of claim 17, wherein the beach is located between a desired beach region and a discharge end of the separator deck further comprising adjusting the conditions of the vibratory separator to move the beach closer to the desired beach region.

* * * * *